United States Patent
Reydel

(10) Patent No.: US 11,278,268 B2
(45) Date of Patent: Mar. 22, 2022

(54) ENDOSCOPY TOOLS AND METHODS OF USE

(71) Applicant: INVENTIO LLC, West Caldwell, NJ (US)

(72) Inventor: Boris Reydel, West Caldwell, NJ (US)

(73) Assignee: INVENTIO LCC, West Caldwell, NJ (US)

( * ) Notice: Subject to any disclaimer, the term of this patent is extended or adjusted under 35 U.S.C. 154(b) by 0 days.

(21) Appl. No.: 16/997,749

(22) Filed: Aug. 19, 2020

(65) Prior Publication Data
US 2020/0375586 A1 Dec. 3, 2020

Related U.S. Application Data

(60) Provisional application No. 62/973,055, filed on Sep. 16, 2019.

(51) Int. Cl.
*A61B 17/00* (2006.01)
*A61B 17/32* (2006.01)
(Continued)

(52) U.S. Cl.
CPC ........ *A61B 17/00234* (2013.01); *A61B 17/32* (2013.01); *A61M 25/0147* (2013.01); *A61B 2017/00296* (2013.01); *A61M 2025/0163* (2013.01); *A61M 2025/024* (2013.01); *A61M 2210/1042* (2013.01)

(58) Field of Classification Search
CPC ... A61B 1/00085; A61B 17/0218; A61B 1/32; A61B 17/221; A61B 1/0008; A61B 1/00087; A61B 1/00154; A61B 1/04; A61B 2017/00269; A61B 2019/1407; A61B 17/00234; A61B 17/32056; A61B 1/00149; A61B 1/01; A61B 1/0125; A61B 1/018
See application file for complete search history.

(56) References Cited

U.S. PATENT DOCUMENTS 1,556,355 A   10/1925  Roney
3,739,784 A *  6/1973  Itoh .................. A61B 1/018
                                          606/113
(Continued)

FOREIGN PATENT DOCUMENTS

JP       2006192086       7/2006

OTHER PUBLICATIONS

"EndoVive™ Enteral Access Devices" available online at https://www.bostonscientific.com/content/dam/bostonscientific/endo/portfolio-group/EndoVive/EndoVive-Family-Brochure.pdf>, 18 pages, Jul. 25, 2017, Retrieved from the Internet Archive Wayback Machine < https://archive.org/web/> on Sep. 23, 2020.
(Continued)

*Primary Examiner* — Scott J Medway
(74) *Attorney, Agent, or Firm* — Meunier Carlin & Curfman LLC

(57) ABSTRACT

The endoscopy tool and methods of use disclosed herein are used to move gastrointestinal tissue. The endoscopy tool includes an auxiliary gastrointestinal device, or a catheter, having a proximal region and a distal region. The endoscopy tool includes a non-conductive, polymeric loop coupled to and extending distally from the distal end of the gastrointestinal device. The surfaces of the loop are smooth such that the loop can move intestinal tissue without causing lacerations.

21 Claims, 9 Drawing Sheets

(51) Int. Cl.
    *A61M 25/01* (2006.01)
    *A61M 25/02* (2006.01)

(56) References Cited

U.S. PATENT DOCUMENTS

| | | | |
|---|---|---|---|
| 4,198,960 A | 4/1980 | Utsugi | |
| 4,250,873 A | 2/1981 | Bonnet | |
| 4,825,259 A | 4/1989 | Berry, Jr. | |
| 5,047,848 A | 9/1991 | Krauter | |
| 5,078,716 A * | 1/1992 | Doll | A61B 18/14 |
| | | | 606/47 |
| 5,084,054 A * | 1/1992 | Bencini | A61B 17/2909 |
| | | | 606/113 |
| 5,122,147 A * | 6/1992 | Sewell, Jr. | A61B 17/32056 |
| | | | 606/110 |
| 5,259,366 A * | 11/1993 | Reydel | A61B 1/00135 |
| | | | 383/203 |
| 5,318,564 A * | 6/1994 | Eggers | A61B 18/1233 |
| | | | 606/47 |
| 5,336,227 A * | 8/1994 | Nakao | A61B 17/32056 |
| | | | 600/106 |
| 5,358,496 A | 10/1994 | Ortiz et al. | |
| 5,387,219 A * | 2/1995 | Rappe | A61B 17/1214 |
| | | | 606/1 |
| 5,417,684 A * | 5/1995 | Jackson | A61B 17/00234 |
| | | | 606/1 |
| 5,486,182 A * | 1/1996 | Nakao | A61B 17/32056 |
| | | | 600/37 |
| 5,535,759 A * | 7/1996 | Wilk | A61B 1/015 |
| | | | 128/898 |
| 5,716,321 A | 2/1998 | Kerin et al. | |
| 5,759,187 A * | 6/1998 | Nakao | A61B 1/015 |
| | | | 606/110 |
| 5,814,052 A | 9/1998 | Nakao et al. | |
| 5,846,248 A * | 12/1998 | Chu | A61B 17/221 |
| | | | 606/114 |
| 5,873,815 A | 2/1999 | Kerin et al. | |
| 5,906,620 A * | 5/1999 | Nakao | A61B 17/12013 |
| | | | 606/113 |
| 5,961,526 A * | 10/1999 | Chu | A61B 17/32056 |
| | | | 606/113 |
| 6,001,111 A * | 12/1999 | Sepetka | A61B 17/122 |
| | | | 606/158 |
| 6,007,546 A | 12/1999 | Snow et al. | |
| 6,015,415 A * | 1/2000 | Avellanet | A61B 18/14 |
| | | | 606/110 |
| 6,093,195 A * | 7/2000 | Ouchi | A61B 18/14 |
| | | | 604/22 |
| 6,123,665 A * | 9/2000 | Kawano | A61B 17/3478 |
| | | | 600/104 |
| 6,537,273 B1 * | 3/2003 | Sosiak | A61B 18/14 |
| | | | 606/170 |
| 6,616,659 B1 * | 9/2003 | de la Torre | A61B 18/085 |
| | | | 128/898 |
| 6,852,111 B1 * | 2/2005 | Lieber | A61B 18/10 |
| | | | 606/113 |
| 7,135,018 B2 * | 11/2006 | Ryan | A61B 18/14 |
| | | | 606/48 |
| 7,282,055 B2 * | 10/2007 | Tsuruta | A61B 17/221 |
| | | | 606/127 |
| 7,485,092 B1 | 2/2009 | Stewart et al. | |
| 7,559,934 B2 * | 7/2009 | Teague | A61B 17/221 |
| | | | 606/113 |
| 7,789,881 B2 * | 9/2010 | Weitzner | A61B 18/14 |
| | | | 606/47 |
| 8,216,234 B2 * | 7/2012 | Long | A61B 18/1477 |
| | | | 606/50 |
| 8,282,572 B2 * | 10/2012 | Bilsbury | A61B 17/00234 |
| | | | 600/562 |
| 8,435,237 B2 * | 5/2013 | Bahney | A61B 18/10 |
| | | | 606/45 |
| 9,498,238 B2 * | 11/2016 | Smith | A61B 18/14 |
| 9,943,665 B2 | 4/2018 | Vaieti et al. | |
| 10,653,428 B2 * | 5/2020 | Khan | A61B 17/08 |
| 10,675,058 B2 * | 6/2020 | Prior | A61B 17/42 |
| 10,758,117 B2 | 9/2020 | Reydel et al. | |
| 10,799,261 B2 * | 10/2020 | Nolan | A61B 17/320016 |
| 2001/0041874 A1 * | 11/2001 | Reydel | A61M 25/0043 |
| | | | 604/266 |
| 2004/0059345 A1 * | 3/2004 | Nakao | A61B 17/221 |
| | | | 606/113 |
| 2004/0138587 A1 * | 7/2004 | Lyons, IV | A61B 17/00234 |
| | | | 600/562 |
| 2005/0125004 A1 | 6/2005 | Bates et al. | |
| 2005/0267332 A1 | 12/2005 | Paul et al. | |
| 2007/0016225 A1 * | 1/2007 | Nakao | A61B 17/221 |
| | | | 606/114 |
| 2007/0208339 A1 * | 9/2007 | Arts | A61B 17/32056 |
| | | | 606/47 |
| 2008/0065122 A1 * | 3/2008 | Stack | A61F 5/0086 |
| | | | 606/151 |
| 2009/0054884 A1 | 2/2009 | Farley et al. | |
| 2010/0023005 A1 | 1/2010 | Yamamoto et al. | |
| 2010/0094327 A1 | 4/2010 | Milsom et al. | |
| 2011/0224492 A1 * | 9/2011 | Stern | A61B 1/018 |
| | | | 600/153 |
| 2011/0251454 A1 | 10/2011 | Robb et al. | |
| 2013/0231534 A1 | 9/2013 | Piskun et al. | |
| 2014/0142393 A1 | 5/2014 | Piskun et al. | |
| 2014/0288377 A1 | 9/2014 | Worrel | |
| 2015/0018616 A1 | 1/2015 | Kumoyama | |

OTHER PUBLICATIONS

"Snares," available online at: <https://diagmed.healthcare/wp-content/uploads/2018/08/Snares-Master-Catalogue.pdf>, 11 pages, Aug. 28, 2019, Retrieved from the Internet Archive Wayback Machine < https://archive.org/web/> on Sep. 23, 2020.

"Cantel Snare", available online at: <https://www.facebook.com/CantelUK/photos/our-unique-'resection-master'-flat/1693034764095985/>, 1 page, Apr. 19, 2018, Retrieved from Facebook <www.facebook.com> on Sep. 23, 2020.

"Overstitch™," available online at: <https://www.overstitch.com/overstitch>, Feb. 20, 2019, Retrieved from the Internet Archive Wayback Machine <https://archive.org/web/> on Sep. 23, 2020.

Weill Cornell Medical College and NewYork-Presbyterian Hospital License Technology to Lumendi, Ltd., Sep. 11, 2015, 3 pages.

Olympus America, Distal Attachments, Jan. 4, 2018, 2 pages.

International Search Report and Written Opinion issued in International Application No. PCT/US2018/18275, dated May 8, 2018.

Extended European Search Report issued for Application No. 18753987.9, dated Aug. 21, 2020.

* cited by examiner

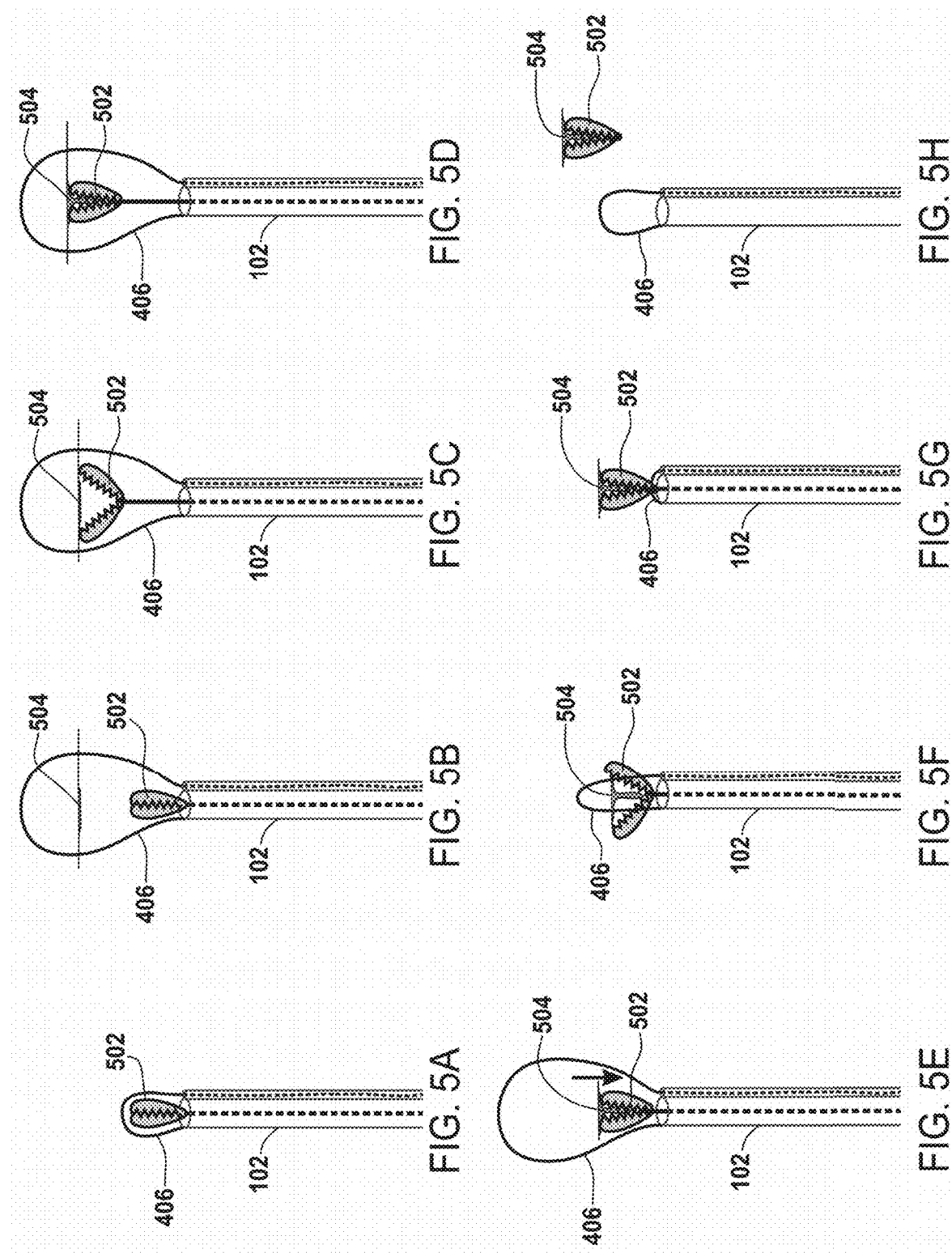

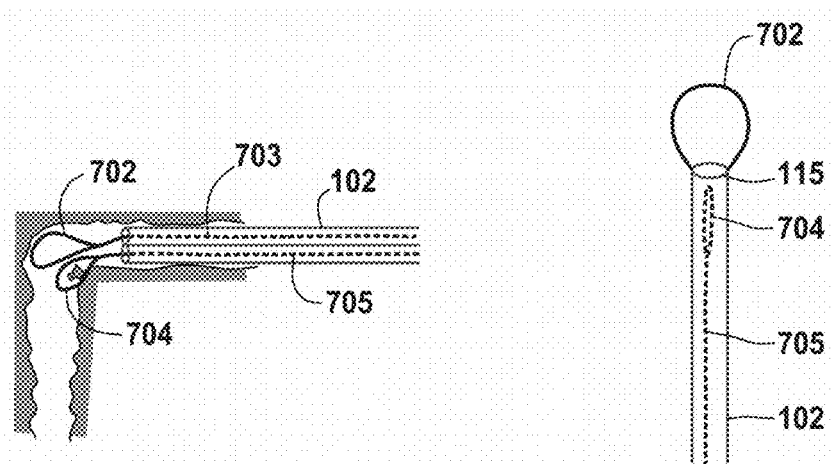

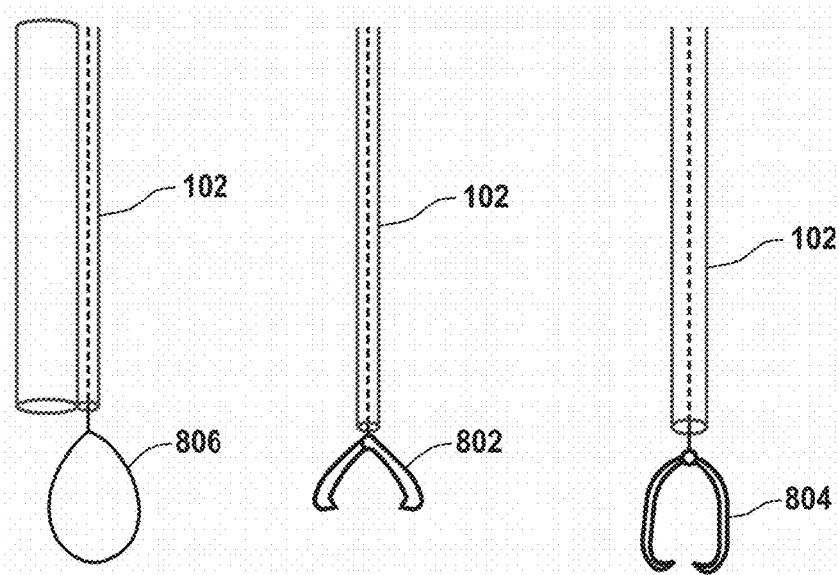

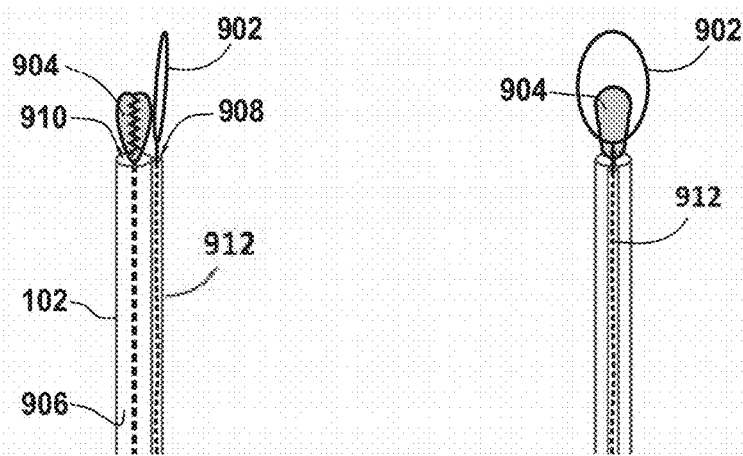

ENDOSCOPY TOOLS AND METHODS OF USE

RELATED APPLICATIONS

This application claims the benefit of U.S. Provisional Patent Application Ser. No. 62/973,055, filed Sep. 16, 2019 and entitled TRANS-SCOPE ENDOSCOPIC FOLD-FLATTENING DEVICE, which is incorporated by reference herein in its entirety and for all purposes.

TECHNICAL FIELD

The present apparatus and method relates, in general, to medical devices and in particular to endoscopy.

BACKGROUND

Endoscopes are well-known in the art and are flexible devices that are inserted into a natural body orifice such as the mouth or anus to provide visual and surgical access to portions of the upper and lower gastrointestinal (GI) tract. Endoscope accessible portions of the lower GI tract, for example, extend from the anus to the small intestine, and during this journey, the flexible endoscope must traverse a torturous, collapsed path through the anus, the rectum, and through the large intestine to the ileocecal opening of the small intestine. The torturous path includes an "S" shaped passage through the rectosigmoid junction and the sigmoid colon, and around several angulations of the splenic flexure and hepatic flexure. Additionally, in small bowel endoscopy, an endoscope must traverse a large torturous convoluted path having multiple "S" shaped passages.

Before insertion of the endoscope, the patient is given drugs to purge matter from the GI tract. Once emptied, the tubular walls of the large intestine can flatten or collapse together into a flattened tubular configuration. The collapsed intestines may inhibit passage of the flat face of the distal end of the endoscope, and the collapsed tissue can inhibit visualization by pressing against or near to a camera mounted within the flat face. To enhance the passage of the endoscope through the collapsed lumen and to improve visualization, insufflation gas is routinely pumped into the patient's GI tract to expand and distend the collapsed tubular tissues. This is the case for both upper and lower GI tract endoscopic procedures. The expanded walls improve visualization and reduce tissue contact with the flat face of the endoscope as it is pushed farther and farther into the insufflated GI tract. The distal portion of the endoscope is steerable, and the insufflated lumen can provide room for the surgeon to visually steer the endoscope through the path ahead.

While insufflation enables the practitioner to better visualize the internal anatomy, it introduces a number of risks to the patient while also increasing the time and cost associated with the endoscopic procedure. The administration of insufflation gas is painful and can cause lengthening of the anatomy and spontaneous perforation. Patients are anesthetized during the procedure and require recovery time, while in the care of the medical facility, to awaken from the anesthesia and purge the insufflation gas. $CO_2$ is commonly used for insufflation as it is more readily absorbed through the patient's intestinal wall to reduce the post-operative recovery time. $CO_2$ gas control systems, $CO_2$ tanks, and $CO_2$ gas heaters must be purchased and maintained in order to provide $CO_2$ as an insufflation gas, adding to the expense of the procedure.

Presently catheters and other gastrointestinal instruments are not capable of easily traversing bends within a gastrointestinal cavity. Gastrointestinal instruments often cause abrasions within the gastrointestinal cavity when performing therapeutic operations in a gastrointestinal cavity. Further, excessive bleeding is caused in operations where gastrointestinal tissue is removed from the gastrointestinal cavity using gastrointestinal instruments.

SUMMARY

Various implementations include a method of moving gastrointestinal tissue. The method includes positioning a gastrointestinal endoscope within a gastrointestinal cavity. The method includes advancing an auxiliary gastrointestinal device through an operative channel of the endoscope. The method includes moving a gastrointestinal tissue using a polymeric, non-conductive loop. The non-conductive loop is coupled to and extends distally from the distal end of the gastrointestinal device. Movement of the gastrointestinal tissue using the loop does not lacerate the tissue. In some implementations, a base of the loop is secured to the distal region of the gastrointestinal device such that axial movement of the gastrointestinal device results in axial movement of the non-conductive loop. In some implementations, the gastrointestinal device is a catheter. In some implementations, the method includes sliding a push wire within a lumen of the catheter. The push wire is coupled to a base of a conductive loop. In some implementations, the method includes axially sliding a push wire within a lumen of the catheter. A base of the non-conductive loop is coupled to, or is an extension of, the push wire such that axial movement of the push wire enables sliding axial movement of the non-conductive loop within the catheter lumen. In some implementations, the method includes expanding the non-conductive loop as it exits the distal end of the catheter. In some implementations, the method includes changing the length of the non-conductive loop extending distally from the distal end of the catheter.

In some implementations, changing the length of the non-conductive loop includes moving one end of the push wire axially within the lumen while holding the other end of the push wire in place. In some implementations, the method includes temporarily stabilizing the tissue by encircling the tissue with the non-conductive loop. In some implementations, the method includes performing a therapeutic procedure using an instrument. In some implementations, the method includes advancing the non-conductive loop through a first lumen of the catheter and advancing the instrument through a second lumen of the catheter. In some implementations, the therapeutic procedure includes pushing distally on the tissue with the non-conductive loop and pulling the tissue proximally through the non-conductive loop using a grasping instrument. In some implementations, the method includes tightening the non-conductive loop around the tissue. In some implementations, the therapeutic procedure includes deploying a detachable clip to secure the gastrointestinal tissue in a folded configuration. In some implementations, the gastrointestinal tissue is folded such that the serosal tissue of one area of the fold contacts the serosal tissue of another area of the fold. In some implementations, the method includes cutting the tissue with a cutting instrument while lifting the cut tissue flap with the non-conductive loop. In some implementations, the method includes moving the cutting instrument independently of the non-conductive loop. In some implementations, the method includes temporarily tightening the non-conductive loop around a tissue to create a raised tissue region. The method includes stabilizing a base of the raised tissue region with the non-conductive loop. The method includes, cutting and cauterizing the raised tissue region using a conductive loop. In some implementations, temporarily tightening the non-conductive loop around the raised tissue region temporarily decreases blood supply to the raised tissue region. In some implementations, the method includes loosening the non-conductive loop at the base of the raised tissue region. The method includes observing bleeding at the base of the raised tissue region. The method includes removing the non-conductive loop from the base of the raised tissue region when bleeding has slowed.

Various other implementations include a gastrointestinal endoscopy system. The system includes an auxiliary gastrointestinal device having a proximal region and a distal region. The system includes a polymeric, non-conductive loop coupled to and extending distally from the distal end of the gastrointestinal device. The surfaces of the non-conductive loop are smooth such that the non-conductive loop can move intestinal tissue without causing lacerations. In some implementations, the gastrointestinal device is a catheter. In some implementations, a base of the non-conductive loop is secured to the distal region of the gastrointestinal device such that axial movement of the gastrointestinal device results in axial movement of the loop. In some implementations, the system includes at least one additional non-conductive loop coupled to and interlocking with the first non-conductive loop. The first plane extends through the first non-conductive loop and intersects an additional plane extending through the additional non-conductive loop. In some implementations, the gastrointestinal device is a catheter, and the non-conductive loop is collapsible and retractable into a lumen of the catheter. In some implementations, the length of the non-conductive loop outside the catheter is variable. In some implementations, the system includes a push wire extending axially within the catheter lumen. A base of the non-conductive loop is coupled to, or is an extension of, the push wire such that sliding axial movement of the push wire enables sliding axial movement of the non-conductive loop within the catheter lumen. In some implementations, the system includes a second nonconductive loop. The base of the second loop is secured to the distal region of the catheter such that axial movement of the catheter results in axial movement of the second loop. In some implementations, the system includes an instrument that is axially slidable relative to the loop. In some implementations, the gastrointestinal device is a catheter having a first lumen. The loop is collapsible and retractable into the first lumen, and the instrument extends within a second lumen of the catheter. In some implementations, the instrument is a cutting instrument. The cutting instrument is conductive or includes a cutting edge. In some implementations, the cutting instrument is a conductive needle knife. In some implementations, the cutting instrument is a conductive loop. In some implementations, the instrument is a grasping instrument configured to grasp and pull intestinal tissue. In some implementations, the instrument is configured to hold the intestinal tissue in the form of a created pseudo-fold. In some implementations, the grasping instrument includes a detachable clip. In some implementations, the system also includes a first grasping instrument configured to initiate invagination, and a second grasping instrument configured to permanently fixate a pseudo-fold of intestinal tissue. In some implementations, the first grasping instrument is smaller than the second grasping instrument. In some implementations, the system includes a gastrointestinal endoscope. The endoscope includes an operative channel. The endoscope includes an auxiliary gastrointestinal device slidably disposed within the operative channel of the endoscope. The gastrointestinal device has a proximal region and a distal region. The gastrointestinal device has a non-conductive, polymeric loop coupled to and extending distally from the distal end of the gastrointestinal device. The surfaces of the loop are smooth such that the loop can move intestinal tissue without causing lacerations. In some implementations, the gastrointestinal endoscope has a length from 60 cm to 300 cm between a proximal end and a distal end. In some implementations, a base of the loop is secured to the distal region of the gastrointestinal device such that axial movement of the gastrointestinal device results in axial movement of the loop. In some implementations, the loop is collapsible and retractable into a lumen of the gastrointestinal device. In some implementations, the system includes an instrument that is axially slidable relative to the loop.

BRIEF DESCRIPTION OF THE DRAWINGS

FIGS. 5A-5H show a method of using an endoscopy tool according to another implementation. FIG. 5A shows a loop coupled to a distal end of the catheter and extending proximally into a lumen of the catheter, and an endoscopic clip emerging from a separate lumen and beyond the distal end of the catheter. FIG. 5B shows the loop being further extended and surrounding a relatively flat polyp in a gastrointestinal tract. FIG. 5C shows the clip opened and positioned around the gastrointestinal tissue. FIG. 5D shows the clip clamped onto and pulling the tissue through the open loop towards the face of the endoscope and creating a pseudo-fold. FIG. 5E shows the clip being further retracted toward the endoscope while pulling the pseudo-fold as the loop stabilizes the surrounding tissue. FIG. 5F shows the loop being closed around the pseudo-fold while compressing and thinning the base of the pseudo-fold with the loop. FIG. 5G shows the clip re-clipped onto the pseudo-fold that has been compressed by the loop (after the loop has been retracted). FIG. 5H shows the clip separated with the loop retracted.

FIG. 6A shows a first loop extending distally from the lumen beyond the distal end of the catheter and surrounding un-raised gastrointestinal tissue. FIG. 6B shows the first loop tightened around the tissue and raising the tissue and the second loop being placed around the raised tissue. FIG. 6C shows the first loop further raising the tissue. FIG. 6D shows the second loop being tightened around the raised tissue. FIG. 6E shows the second loop cutting the raised tissue while the first loop continues to hold the base of the tissue.

FIGS. 7A-7B show a method of using the endoscopy tool according to another implementation. FIG. 7A shows two loops being used to perform a procedure near a bend in the gastrointestinal cavity. FIG. 7B shows another implementation of an endoscopy tool having a first loop extending distally from the lumen, beyond the distal end of the catheter.

FIGS. 8A-8B show the endoscopy tool according to another implementation. FIG. 8A shows the endoscopy tool with a loop grasper. FIG. 8B shows the endoscopy tool having a first grasper clip. FIG. 8C shows the endoscopy tool having a second grasper clip.

FIGS. 9A-9B show the endoscopy tool according to another implementation. FIG. 9A shows a front view of the endoscopy tool having a loop and a grasper, where the loop and the grasper are each disposed in a separate lumen of a catheter. FIG. 9B shows a side view of the endoscopy tool shown in FIG. 9A.

DETAILED DESCRIPTION

Figure 1:
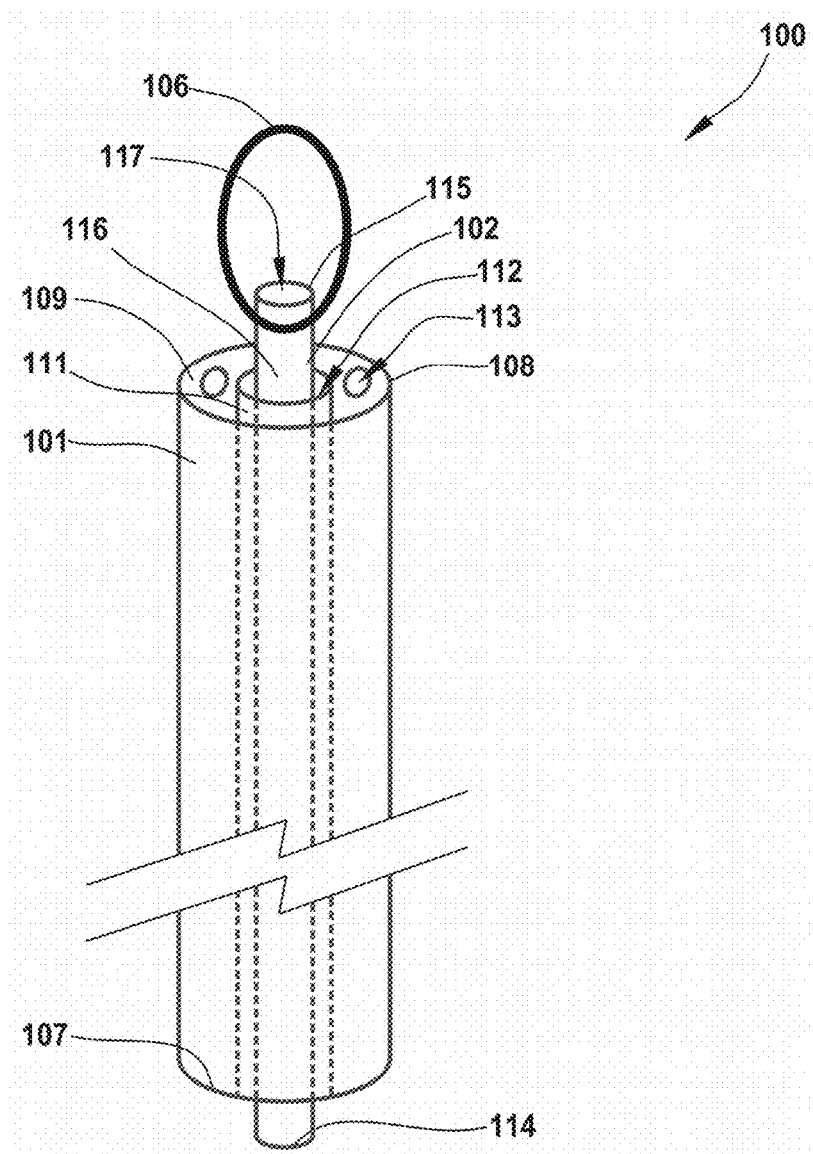
FIG. 1 shows a gastrointestinal endoscopy system according one implementation, having a loop coupled to the tip of a catheter.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of the endoscope or the endoscopic catheter. "Proximal" means a region closest to the practitioner during a procedure, while "distal" means a region farther from the from the practitioner during a procedure.

The methods devices and systems for moving gastrointestinal tissue facilitate the movement of gastrointestinal tissue during a gastrointestinal procedure. The nonabrasive wire loops disclosed herein provide a non-abrasive method of guiding a catheter in a gastrointestinal cavity and securing the tissue without causing abrasions and damage to the gastrointestinal cavity. This application incorporates U.S. patent application Ser. No. 15/897,320 by reference in its entirety, which pertains to Endoscopic Assistance Devices and Methods of Use.

Multiple gastrointestinal instruments in a catheter such as loops, clips, and graspers, provides a method of occluding blood flow during procedures requiring removal of gastrointestinal tissue.

Gastrointestinal endoscopy systems such as the systems shown in FIGS. 1-8 are disclosed herein. According to one implementation, as shown in FIG. 1, a gastrointestinal endoscopy system 100 includes a gastrointestinal endoscope 101, an auxiliary gastrointestinal device such as catheter 102, and a non-conductive, polymeric loop 106. The loop 106, being coupled and extending distally from distal end 115 of the catheter 102, provides a tool that can move or isolate a mass of tissue in areas not reachable by other tools which do not track the trajectory of a gastrointestinal instrument such as a catheter.

The gastrointestinal endoscope 101 is a flexible cylindrical body having a proximal end 107, a distal end 108, and a tube wall 109. The endoscope 101 is flexible such that a physician can advance the endoscope 101 through a patient's gastrointestinal tract while the endoscope conforms to curvature in the patient's gastrointestinal tract. The tube wall 109 has an outer surface and an inner surface 111 separated from the outer surface 109 by a wall width. The inner surface 111 defines an operative channel 112. The operative channel extends from the proximal end 107 of the gastrointestinal endoscope 101 to the distal end 108 of the gastrointestinal endoscope 101. The operative channel 112 has a circumference that is large enough to advance the catheter 102 therethrough. The gastrointestinal endoscope 101 can have additional features 113 disposed in the width of the tube wall 109. For example, the additional features 113 can be light sources or channels for air, water, or other fluids.

Loop 106 is coupled to and extends distally from an auxiliary gastrointestinal device, such as the catheter 102 shown in the embodiment of FIG. 1. The catheter 102 is a flexible cylindrical body having a proximal end 114 and distal end 115, and tube wall 116 that extends between the proximal end 114 and the distal end 115 of the catheter 102. The tube wall 116 has an inner surface that defines a lumen 117. The catheter 102 is sufficiently flexible to navigate curves within the operative channel 112 of the endoscope 101. The catheter 102 has a proximal region which spans between the proximal end 114 of the catheter 102 and an axial midpoint of the catheter 102. The catheter also has a distal region 102g that extends between the midpoint 102f of the catheter and the distal end 102b of the catheter 102. Catheter length, as measured between proximal end 114 and distal end 115, can be adapted to suit the procedure and the type of endoscope used for the procedure. For example, in some embodiments a catheter used for a gastrointestinal procedure can be anywhere from about 60 cm to about 300 cm long, including, for example, about 60 cm, about 80 cm, about 100 cm. The catheter 102 shown in FIGS. 1-8 has a single lumen. But, in some implementations, the catheter 102 has a plurality of lumens, such that a plurality of endoscopy instruments can be advanced through a respective lumen as shown in FIG. 8. The catheter 102 can be formed from any material suitable for use with a gastrointestinal endoscopy catheter.

The loop 106 shown in FIG. 1 is formed from a non-conductive, polymeric wire or cord configured as an oval loop and bonded or securely coupled to the distal region or distal end 115 the catheter 102. The wire is flexible and retains its shape when not under load, such that a practitioner can manipulate the wire (for example, compress it to insert it through operative channel 112), and it will resiliently return to its previous oval shape once it exits the operative channel. The shape and dimensions of the loop 106 can be manipulated by pressing sides of the loop to reshape it. The loop 106 has a smooth surface such that the surface of the loop 106 does not cause lacerations when sliding along bodily tissue such as gastrointestinal tissue. The loop 106 can be formed from any variety of non-conductive polymeric materials, such as, but not limited to, polyurethane (such as Isoplast® 2510 or Pellethane®, for example).

The loop 106 is securely coupled to the catheter 102 such that axial movement of the catheter results in axial movement of the loop 106. The catheter 102 is disposed inside the operative channel 112 of the endoscope 101 and can be advanced through the operative channel 112. The proximal end 114 of the catheter 102 extends beyond the proximal end 107 of the endoscope 101. And, the distal end 115 of the catheter 102 extends beyond the distal end 108 of the endoscope 101 when in an operational position.

The gastrointestinal endoscopy system shown in FIG. 1 shows an oval loop bonded to the catheter 102 near the distal end 115. But in other implementations, the loop is formed from a non-conductive, polymeric wire or cord having two ends each securely coupled near or at the distal end 115 of the catheter 102. The ends of the loop are fixedly coupled to the distal end of the catheter, such that a wire having a fixed length forms the loop with the distal end 115 of the catheter 102.

The gastrointestinal endoscopy system shown in FIG. 1 shows a catheter 102, but in other implementations, the loop 106 can be coupled to a distal end of any auxiliary gastrointestinal device including, but not limited to biopsy forceps, a coagulation catheter, a sclerotherapy needle, a needle knife, or any other gastrointestinal instrument suitable for being advanced into a patient's gastrointestinal tract.

Figure 2:
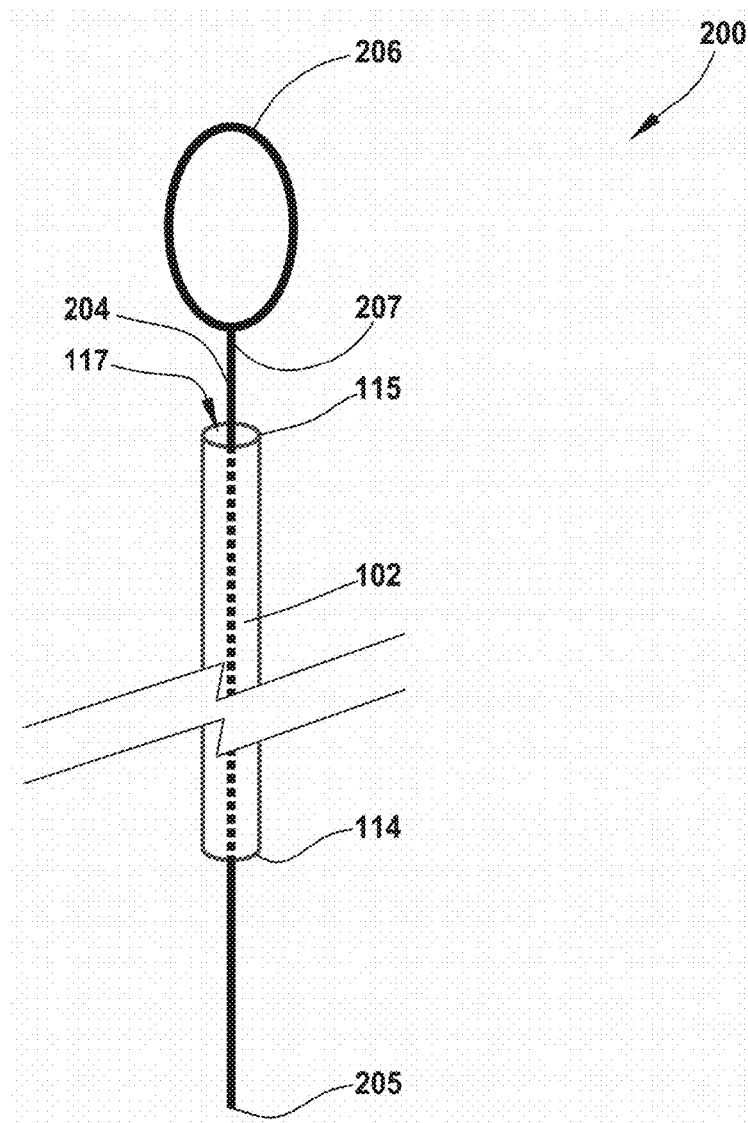
FIG. 2 shows an endoscopy tool according to another implementation having a loop coupled to a push wire that extends through a lumen of the catheter.

FIG. 2 shows a gastrointestinal endoscopy system 200 according to another implementation. The system 200 includes the catheter 102 as described above. The system also includes a loop 206. The loop 206 is a closed loop, which is coupled to a distal end of a push wire 204 at a base the loop 206. The loop is formed from non-conductive plastic. The push wire 204 has a proximal end 205 and a distal end 207. The push wire 204 extends at least partially within the lumen 117 of the catheter 102. The push wire 204 can be formed from conductive or non-conductive materials. The proximal end 205 of the push wire 204 extends beyond the proximal end 114 of the catheter 102, and the distal end 207 of the push wire 204 extends beyond the distal end 115 of the catheter 102 such that the loop 206 can be manipulated by a physician at the proximal end 114 of the catheter 102. The loop 206 is rigidly attached to the push wire 204 such that axial sliding the push wire 204 within the lumen 117 results in axial sliding of the loop 206 beyond the distal end 115 of the catheter 102. In some implementations, the push wire 204 and the loop 206 are formed from separate wires bonded or welded at the base of loop 206. In other implementations, the push wire and the loop are formed from a single wire with a loop formed at a distal end of the single wire. A proximal end of the single wire extends away from the loop 206 to form push wire 204. In such implementations, the distal end of the single wire is curled toward itself forming loop 206.

Some embodiments can include more than one loop attached or axially slidable within a catheter 102. The loops can all be non-conductive, can all be conductive, or can be a combination of conductive and non-conductive. For example, a first loop may be coupled near distal end 115 of a catheter 102 as shown in FIG. 1, and a second loop may be positioned on a push wire and axially slidable within lumen 117 of catheter 102 as shown in FIG. 2. Such an example is shown in FIG. 7A. Or, a single catheter can have multiple loops affixed near the distal end. Alternatively, a single catheter may have two separate loops, each attached to its own push wire, and both axially slidable within catheter lumen 117 as shown in FIG. 7B. The push wire 204 can be formed from metal or plastic and can be conductive or non-conductive.

Figure 3:
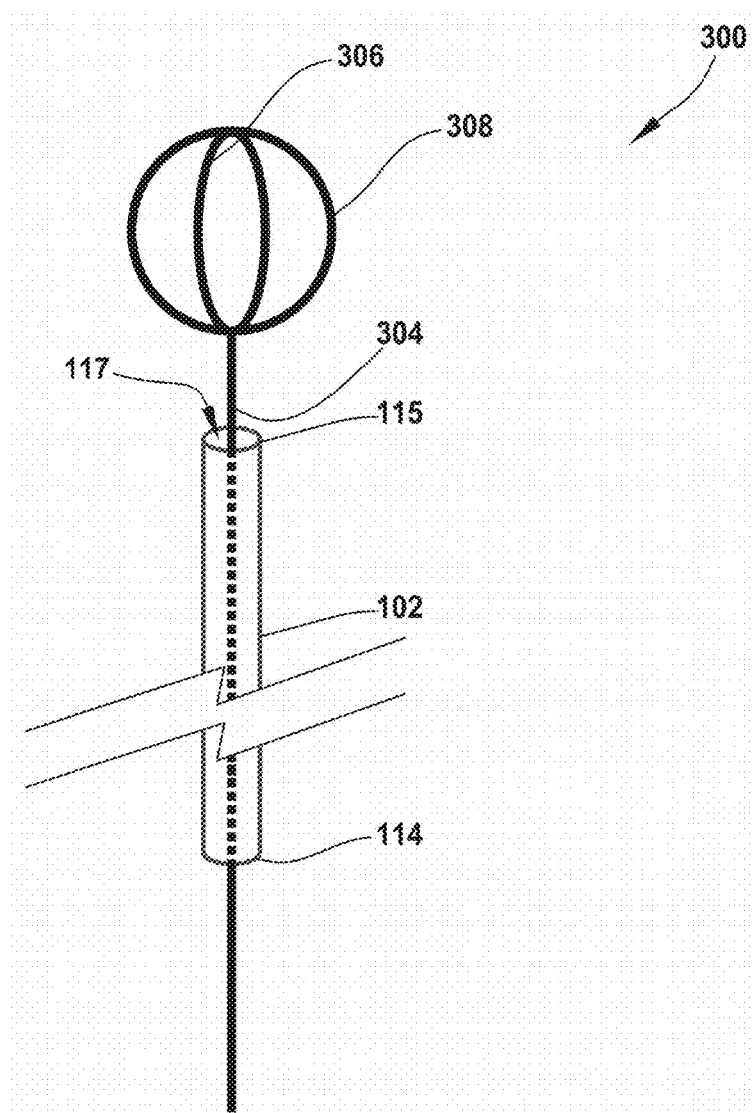
FIG. 3 shows an endoscopy tool according to another implementation having two loops coupled to a wire that extends through a lumen of the catheter

FIG. 3 shows another implementation of a gastrointestinal endoscopy system, including catheter 102 described above. The system also includes a first loop 306, a second loop 308 coupled to the first loop, and a push wire 304 which is coupled to the first loop 306 and the second loop 308 and extends proximally therefrom. The first loop 306 is disposed in a first plane and the second loop 308 is disposed in a second plane. The first loop 306 and the second loop 308 are positioned such that the first plane and the second plane intersect each other when the first loop 306 and the second loop 308 are each extended beyond the distal end of the catheter 102. The first loop 306 and the second loop 308 interlock with each other such that axial and rotational translation of the first loop 306 effects axial and rotational translation of the second loop 308. Although the first loop 306 and the second loop 308 are each disposed in planes that intersect one another, in some implementations, the first loop 306 and the second loop 308 are disposed in the same plane or non-intersecting planes. Although the first loop 306 and the second loop 308 as shown in FIG. 3 share a single wire extending therefrom, in some implementations, a respective first wire and second wire are coupled to and extend from the first loop 306 and the second loop 308. In the implementation of FIG. 3, the first loop 306 and the second loop 308 are coupled together. But, in other implementations, such as the implementation shown in FIGS. 7-8 the first loop and the second loop 308 are not connected and can be axially advanced, retracted, and rotated independently. The second loop 308 as shown in FIG. 3 is formed from any variety of non-conductive polymeric materials, such as, but not limited to, polyurethane (such as Isoplast® 2510 or Pellethane®, for example).

Figure 4:
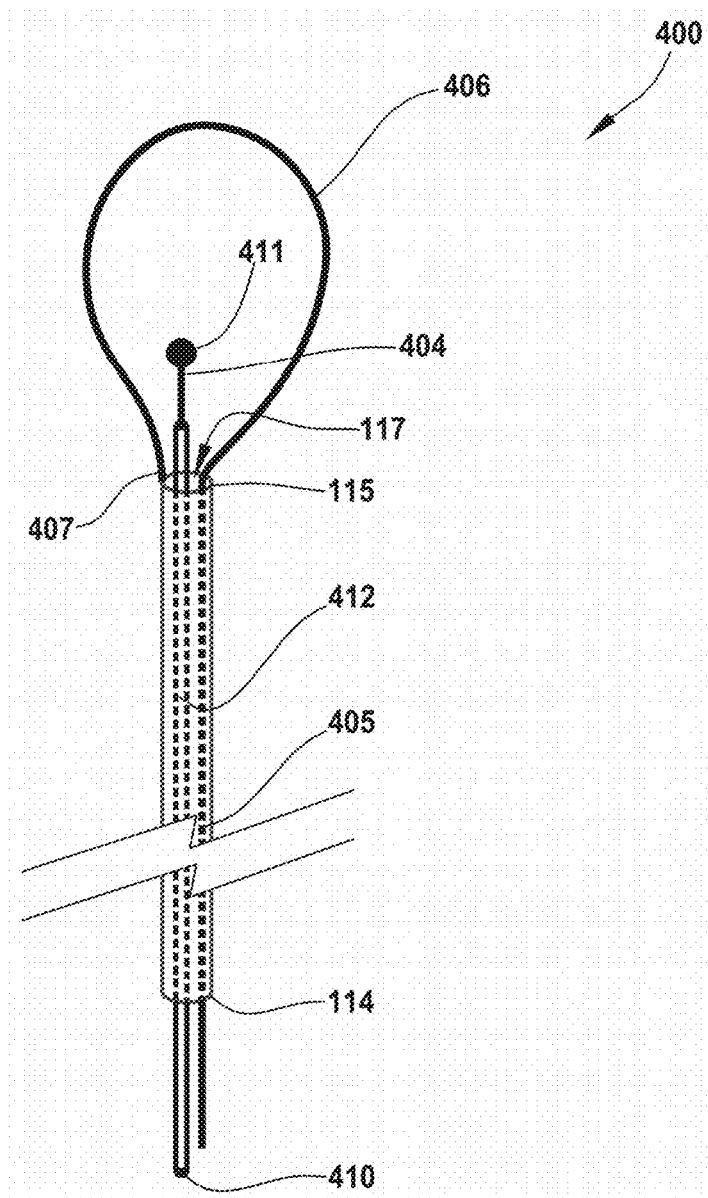
FIG. 4 shows the endoscopy tool according to another implementation, having a loop extending distally from the lumen beyond a distal end of the catheter and a needle knife extending distally from the lumen, beyond the distal end of the catheter.
Figure 6A:
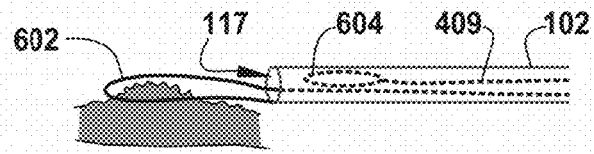
FIGS. 6A-6E show a method of using the endoscopy tool according to another implementation.
Figure 6B:
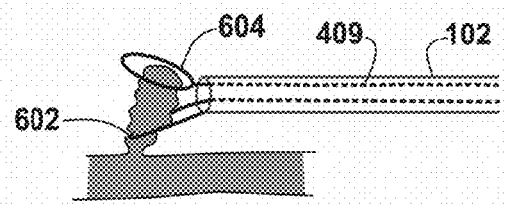
Figure 6C:
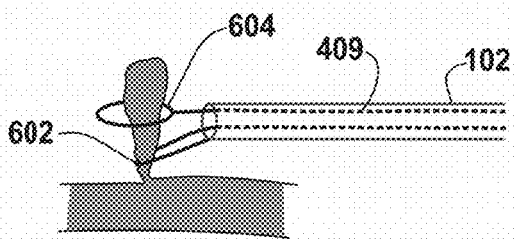
Figure 6D:
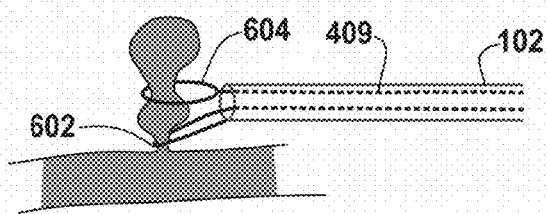
Figure 6E:
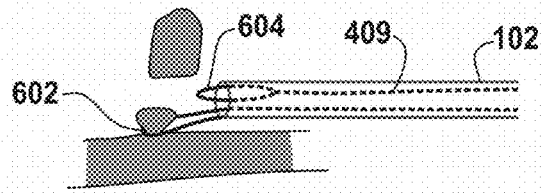

According to another implementation, a gastrointestinal endoscopy system 400 as shown in FIG. 4 includes the catheter 102 described above. The system includes a needle knife 404 formed from a conductive material. The system also includes a loop 406. The loop 406 is formed from a non-conductive cord or wire 405. The cord or wire 405 has a distal end 407 which is coupled to the distal end 115 of catheter 102. The cord or wire 405 extends axially through the lumen 117 of the catheter 102. The proximal end of the cord or wire 405 extends proximally beyond the proximal end 114 of the catheter 102. The size of the loop 406 is adjustable by manipulating the proximal end of the cord or wire 405. The loop 406 has a length in the axial direction and a width in the transverse direction. Both the length and the width of loop 406 can be varied by axial movement of the cord or wire 405 through the lumen 117. That is, a user can pull the cord or wire 405 toward the proximal end 114 of the catheter 102 to reduce the size of the loop 406 and the user can advance the cord or wire 405 toward the distal end 115 of the catheter 102 to increase the size of the loop 406. The loop 406 is collapsible such that the cord or wire 405 can be pulled axially to collapse the loop 406 into the lumen 117 of the catheter 102.

The needle knife 404 has a proximal end 410 and a cutting edge 411. The proximal end 410 and the cutting edge 411 are connected by a rod 412, which extends between the proximal end 410 and the cutting edge 411. The needle knife 404 shown in FIG. 4 can be formed of steel or any other conductive material suitable for forming a gastrointestinal needle knife. The rod 412 is disposed inside the lumen 117 of the catheter 102, and the cutting edge 411 extends distally beyond the distal end of the catheter 102. The needle knife 404 is axially translatable independent of the loop 406, such that the needle knife 404, moves relative to the loop 406. FIG. 4 shows the needle knife 404 disposed in the lumen 117 of the catheter 102. But, in implementations where the catheter 102 has a plurality of lumens, the needle knife 404 or any other gastrointestinal instrument can be disposed in an additional lumen separate from the lumen 117 in which wire 405 is disposed. Furthermore, both ends of loop 406 can be coupled near the distal end of the catheter 115 as in FIG. 1, or loop 406 can be coupled at its base to a push wire as in FIG. 2. FIG. 4 shows a needle knife disposed partially within the lumen 117. But, in other implementations, biopsy forceps, a coagulation catheter, a sclerotherapy needle, a polypectomy snare, endoscopic scissors, or any other gastrointestinal device suitable for being advanced into a patient's gastrointestinal tract can also be disposed in the lumen.

The system can further utilize clips 502 as shown in FIG. 5 which can clamp gastrointestinal tissue in to create a pseudo-fold 504. The clips 502 can pull gastrointestinal tissue through the loop 406 to hold the fold in a stationary position. The clip 502 shown in FIG. 5 is a detachable clip that can open and close multiple times. The clip 502 can function as a grasper and be used to hold tissue in place or occlude blood flow even after the endoscopy system is removed. But, in other implementations, non-detachable clips are utilized in the system. The system can also include grasping instruments 802, 804 as shown in FIG. 8, which grasp and pull gastrointestinal tissue while a loop 806 is pushing it in an opposite direction. Grasping instruments 802, 804 of various sizes can be used and, in some implementations, a first grasping instrument 802 is smaller than a second grasping instrument 804 used in a uniform operation. The first grasping instrument 802 can be used to pinch and thin the gastrointestinal tissue to a desired thickness. The first grasping instrument 802 can be sized such that the second grasping instrument 804 can fit around the smaller grasping instrument 802 while the smaller grasping instrument 802 is coupled to a piece of gastrointestinal tissue. In some implementations, grasping instrument 804 can also be a detachable clip and can be dislodged from the system and left in the tissue as shown in FIG. 5.

According to some implementations, as shown in FIGS. 9A and 9B, a system 900 includes a loop 902, a grasper 904, and a catheter 102 having a first lumen 908 and a second lumen 910. The first lumen 908 is axially offset from the second lumen 910. The grasper 904 is coupled to a push wire 906 which extends at least partially within the second lumen 910. The loop 902 is coupled to a push wire 912 which extends at least partially into the first lumen 908. The grasper 904 can be used as the grasping instruments 802, 804 described above. The loop 902 provides an awning to deflect an intestinal fold or intestinal wall and adjust a trajectory of the catheter 102 as it travels through a gastrointestinal tract.

According to one implementation of a method for moving gastrointestinal tissue, as shown in FIG. 5, an endoscope 101 as described above and illustrated in FIG. 1 is positioned within a gastrointestinal cavity. The endoscope 101 is advanced through the gastrointestinal tract to a procedure site. The catheter 102, having the loop 406 and the clip 502, which is similar to the clip described above are advanced through the operative channel 112 of the endoscope 101. The first loop is disposed in an initial retracted state (FIG. 5A) and in FIG. 5B is expanded to increase the its length as it exits the distal end 115 of the catheter 102, to surround the tissue to be moved. In this example, the tissue is a relatively flat polyp. The loop is expanded by advancing the push wire 104 through the lumen 117 as the second end of the push wire is fixedly coupled to the distal end 115 of the catheter 102. The clip 502 is formed such that it is coupled to an additional wire 503 though the lumen 117. The clip 502 is extended distally away from the distal end of the catheter 102. The clip 502 is actuated proximal of the proximal end of the catheter 102, opening the clip as shown in FIG. 5C and clamped onto the tissue 504 as shown in FIG. 5D. The loop 406 is also being advanced distally in FIG. 5D, pushing against the surrounding tissue as the clip 502 pulls the tissue 504 proximally through loop 406, creating a pseudo-fold. The push wire 503 attached to clip 502 is then pulled proximally within lumen 117, as shown in FIG. 5E, pulling the pseudo-fold more proximally as the surrounding tissue is stabilized by loop 406. The closure of the loop 406 around the tissue 504 pinches and thins the base of the pseudo-fold and secures it as shown in FIG. 5F. The clip 502 is opened a second time as shown in FIG. 5F and can be advanced distally to grasp a greater area of the tissue 504 while the loop 406 holds it steady. This process can be repeated multiple times to create a very deep fold, potentially even pulling the intestinal serosa, the outer layer of the intestinal wall, into the fold. The loop 406 is then fully retracted into catheter lumen 117 while the clip 502 stays in place (FIG. 5G). The clip 502 can then be separated from the catheter 102 and remain clamped to the tissue fold (FIG. 5H). This "serosa-to-serosa" folding can be advantageous as an efficient way to create a permanent fold because the opposing serosal faces form adhesions and/or scar tissue that stabilizes the fold. The loop 406 used in the method is formed from a smooth material that does not lacerate the tissue in the gastrointestinal cavity. Although a loop and clip 502 are shown in FIG. 5, in some implementations, a first grasping instrument and a second grasping instrument are used such as is shown in FIG. 8. The first grasping instrument 802 can be used to initiate invagination of the tissue, and the second grasping instrument 804 can be used to permanently fixate a pseudo-fold in the tissue. The loop 406 and the clip 502 are advanced through the lumen 117 of the catheter 102 in the implementation shown in FIG. 5. But, the loop and the clip can be advanced through separate lumens in implementations utilizing a catheter having additional lumens as discussed above.

According to another implementation as shown in FIG. 6, a catheter 102 is inserted into a patient. Two loops 602, 604 are disposed in the lumen 117 of the catheter 102. The second loop 604 is formed of a conductive material and coupled to a push wire 409. The catheter 102, and the loops 602, 604 disposed therein, are advanced into a patient and the first loop 602 is placed around portion of gastrointestinal tissue while the second loop 604 remains inside the lumen 117 of the catheter 102. The first loop 602 is placed around the tissue and tightened around the tissue to secure it in place and create a raised tissue region. Tightening the first loop 602 around the raised tissue region slows blood flow in the raised tissue region. The first loop 602 is used to stabilize a base of the raised tissue region. The second loop 604 is placed around the tissue at a location 10648-004US1 separated from the location of the first loop 602. While the tissue is secured by the first loop 602, the size of the second loop is reduced to a diameter less than that of the tissue, such that the second loop 604 cuts the raised tissue region. The second loop 604 is formed from steel wire or any other conductive material. The conductive material is heated by electric resistance and cauterizes the raised tissue region as it cuts it with a single cutting motion. The practitioner observes the base of the raised tissue region to determine if the raised tissue region is bleeding. When bleeding has slowed, the first loop 602 is slowly loosened and removed from the base of the raised tissue region. The first loop 602 and the second loop 604 are then retracted into the lumen 117 of the catheter 102 and removed from the patient. In some implementations, the loops 602, 604 are advanced in opposite axial directions to vary the amount of gastrointestinal tissue grasped during the procedure.

Two loops can be used to facilitate some procedures, such as, for example, procedures taking place at or near angulations (or bends) in the intestinal tissue. In the implementation and method shown in FIG. 7A, a single catheter 102 is inserted into a patient. Two loops 702, 704 are disposed in the lumen 117 of the catheter 102 (either in the same catheter lumen, or in separate catheter lumens). According to the implementation shown in FIG. 7A, the first loop 702 deflects, or pushes back, intestinal tissue on the distal side of the bend. The loop 702 allows a practitioner to better observe the region around the bend using the endoscope (endoscope not shown). The first loop 702 may be positioned on a push wire 703 and extended at a distance distal of the distal end 115 of the catheter 102 (as shown in FIG. 7A), or it may be affixed to the distal end of catheter 102 such that axial movement of the catheter 102 results in axial movement of the loop 702 (as shown in FIG. 7B). The non-abrasive surface of the first loop 702 slides along the gastrointestinal tract of a patient and guides the catheter 102 to the bend. The second loop 704 is positioned on a push wire 705 and is extended to the location of the bend and can, in some implementations, be guided by a contour in the first loop 702. The second loop 704 is placed around a segment of gastrointestinal tissue to secure it. In the method shown in FIG. 7A, second loop 704 is being used to secure a polyp. In some implementations, the tissue or polyp can be cut by axially translating a cutting instrument such as a metallic loop (for example, if the second loop 704 is conductive) or the needle knife, as described above, while the tissue of the bend is lifted by first loop 702.

The methods described above contemplate moving and cutting gastrointestinal tissue with gastrointestinal instruments. But, such instruments can be used to perform various therapeutic procedures within a gastrointestinal cavity. In some implementations a procedure includes alternately stabilizing gastrointestinal tissue with a loop and pulling the tissue with a grasping instrument through the loop with a clamp. In other implementations, the procedure includes folding gastrointestinal tissue such that serosal tissue of one area of the fold contacts the serosal tissue of another area of the fold. In other implementations, the method includes placing a loop around a portion of gastrointestinal tissue and manipulating the gastrointestinal tissue by pulling or pushing a push wire coupled to the loop.

The invention claimed is:
1. A method of moving gastrointestinal tissue, the method comprising:
   positioning a gastrointestinal endoscope within a gastrointestinal cavity;
   advancing a catheter through an operative channel of the endoscope;
   pushing a non-conductive wire through a lumen of the catheter, wherein a distal end of the non-conductive wire is fixedly coupled to a distal region of the catheter and a proximal end of the non-conductive wire is movable with respect to the distal end of the non-conductive wire;
   pushing a distal region of the non-conductive wire out of the lumen of the catheter;
   expanding a non-conductive loop formed from the distal region of the non-conductive wire;
   contacting a first region of gastrointestinal tissue with the non-conductive loop;
   moving an instrument relative to the non-conductive loop;
   performing a therapeutic procedure on a second region of gastrointestinal tissue using the instrument, the second region of gastrointestinal tissue adjacent the first region of gastrointestinal tissue; and
   withdrawing the non-conductive loop, the catheter, and the gastrointestinal endoscope from the gastrointestinal cavity;

wherein the non-conductive loop is unattached to the instrument and operates independently from the instrument and wherein the non-conductive loop does not lacerate the tissue.

2. The method of claim 1, further comprising changing the length of the non-conductive loop extending distally from the distal end of the catheter.

3. The method of claim 2, wherein changing the length of the non-conductive loop comprises moving the proximal end of the non-conductive wire axially with respect to the proximal end of the catheter.

4. The method of claim 1, wherein contacting the first region of gastrointestinal tissue further comprises temporarily stabilizing the tissue.

5. The method of claim 4, wherein temporarily stabilizing the tissue comprises encircling the tissue with the non-conductive loop.

6. The method of claim 1, wherein the lumen of the catheter is a first lumen of the catheter, and wherein the instrument occupies a second lumen of the catheter.

7. The method of claim 1, wherein the instrument is a grasping instrument, and wherein the therapeutic procedure comprises pushing distally on the tissue with the non-conductive loop and pulling the tissue proximally through the non-conductive loop using a grasping instrument.

8. The method of claim 7, further comprising tightening the non-conductive loop around the tissue.

9. The method of claim 7, wherein the therapeutic procedure further comprises deploying a detachable clip to secure the gastrointestinal tissue in a folded configuration.

10. The method of claim 9, wherein the gastrointestinal tissue is folded such that serosal tissue of one area of the fold contacts serosal tissue of another area of the fold.

11. The method of claim 1, wherein the instrument is a cutting instrument, and the therapeutic procedure further comprises cutting the tissue with the cutting instrument while lifting the cut tissue flap with the non-conductive loop.

12. The method of claim 1, further comprising moving the instrument while holding the non-conductive loop stationary.

13. The method of claim 1, wherein the instrument is a conductive loop, and the method further comprises temporarily tightening the non-conductive loop around the first region of gastrointestinal tissue to create a base of a raised tissue region, stabilizing the base of the raised tissue region with the non-conductive loop, and cutting and cauterizing the raised tissue region using the conductive loop.

14. The method of claim 13, wherein temporarily tightening the non-conductive loop around the base of the raised tissue region temporarily decreases blood supply to the raised tissue region.

15. The method of claim 13, further comprising loosening the non-conductive loop at the base of the raised tissue region, observing bleeding at the base of the raised tissue region, and removing the non-conductive loop from the base of the raised tissue region when bleeding has slowed.

16. The method of claim 1, further comprising sequentially increasing and reducing a size of the non-conductive loop.

17. A method of moving gastrointestinal tissue, the method comprising:
positioning a system for moving gastrointestinal tissue within a gastrointestinal cavity, the system comprising a gastrointestinal endoscope and an auxiliary gastrointestinal device;
advancing the auxiliary gastrointestinal device through an operative channel of the endoscope;
moving a gastrointestinal tissue using a non-conductive loop that extends distally from a distal region of the auxiliary gastrointestinal device;
moving an instrument relative to the non-conductive loop;
withdrawing the non-conductive loop, the auxiliary gastrointestinal device, and the gastrointestinal endoscope from the gastrointestinal cavity;
wherein the non-conductive loop does not lacerate the tissue;
wherein a coupling of the non-conductive loop to the system for moving gastrointestinal tissue consists of either a fixed attachment of a proximal base of the non-conductive loop to a push wire or a fixed attachment of the proximal base of the non-conductive loop to the auxiliary gastrointestinal device; and
wherein the non-conductive loop is unattached to the instrument and operates independently from the instrument.

18. The method of claim 17, wherein the coupling consists of the fixed attachment of the proximal base of the non-conductive loop to the auxiliary gastrointestinal device, such that axial movement of the auxiliary gastrointestinal device results in axial movement of the non-conductive loop.

19. The method of claim 17, wherein the coupling consists of the fixed attachment of the proximal base of the non-conductive loop to the push wire, the auxiliary gastrointestinal device is a catheter, and the method further comprises advancing the push wire within a lumen of the catheter.

20. The method of claim 19, wherein advancing the push wire advances the non-conductive loop within the lumen of the catheter.

21. The method of claim 17, wherein the auxiliary gastrointestinal device is a catheter, and moving an instrument relative to the non-conductive loop further comprises advancing a conductive loop within a lumen of the catheter.

* * * * *